(12) United States Patent
Lea

(10) Patent No.: US 12,122,701 B2
(45) Date of Patent: Oct. 22, 2024

(54) GASIFICATION AND FISCHER-TROPSCH PROCESS WASTE WATER TREATMENT

(71) Applicant: Velocys Technologies Limited, Oxford (GB)

(72) Inventor: Graham Lea, Cambridgeshire (GB)

(73) Assignee: Velocys Technologies Limited, Oxford (GB)

(*) Notice: Subject to any disclaimer, the term of this patent is extended or adjusted under 35 U.S.C. 154(b) by 0 days.

(21) Appl. No.: 17/912,224

(22) PCT Filed: Mar. 16, 2021

(86) PCT No.: PCT/EP2021/056728
§ 371 (c)(1),
(2) Date: Sep. 16, 2022

(87) PCT Pub. No.: WO2021/185865
PCT Pub. Date: Sep. 23, 2021

(65) Prior Publication Data
US 2023/0202945 A1 Jun. 29, 2023

(30) Foreign Application Priority Data
Mar. 18, 2020 (GB) .................................. 2003906

(51) Int. Cl.
*C01B 3/48* (2006.01)
*B09B 3/40* (2022.01)
(Continued)

(52) U.S. Cl.
CPC .................. *C02F 9/00* (2013.01); *B09B 3/40* (2022.01); *C01B 3/48* (2013.01); *C07C 1/0485* (2013.01);
(Continued)

(58) Field of Classification Search
CPC .............. C01B 3/48; C01B 2203/0255; C01B 2203/0283; C01B 2203/062; C07C 1/0485
See application file for complete search history.

(56) References Cited

U.S. PATENT DOCUMENTS

2005/0187415 A1 8/2005 Lawson et al.
2016/0075579 A1 3/2016 Lea et al.

FOREIGN PATENT DOCUMENTS

CN 106746226 A 5/2017
CN 110272151 A 9/2019
(Continued)

OTHER PUBLICATIONS

Combined Search and Examination Report for related Great Britain Application No. GB2003906.1 dated Sep. 14, 2020.
(Continued)

*Primary Examiner* — Jafar F Parsa
(74) *Attorney, Agent, or Firm* — Renner, Otto, Boisselle & Sklar, LLP

(57) ABSTRACT

In a process for treating wastewater from a combined gasification and Fischer-Tropsch (F-T) process, feedstock derived from Municipal Solid Waste or the like is gasified in a reactor (R) and treated in a cleanup unit (C) which generates a first wastewater stream (1st WWT STREAM) containing salts and inorganic pollutants. The first wastewater stream is treated in a treatment unit (T1) to remove inorganic pollutants derived from the syngas. The treatment comprises a) degassing, and subsequently b) neutralising the first wastewater stream before treatment in a Dissolved Air Flotation unit (72c) and filtering in a moving sand bed or similar (72d) to remove solids, and a stripping process to remove ammonia. A second wastewater stream ($2^{nd}$ WWT Stream) containing organic pollutants but being low in salts (Continued)

arises from the F-T process and is treated separately to allow recycling within the F-T process.

22 Claims, 3 Drawing Sheets

(51) Int. Cl.
| | |
|---|---|
| *C02F 1/00* | (2023.01) |
| *C02F 1/20* | (2023.01) |
| *C02F 1/24* | (2023.01) |
| *C02F 1/28* | (2023.01) |
| *C02F 1/44* | (2023.01) |
| *C02F 1/48* | (2023.01) |
| *C02F 1/52* | (2023.01) |
| *C02F 1/56* | (2023.01) |
| *C02F 1/66* | (2023.01) |
| *C02F 1/72* | (2023.01) |
| *C02F 3/12* | (2023.01) |
| *C02F 9/00* | (2023.01) |
| *C02F 101/10* | (2006.01) |
| *C02F 101/16* | (2006.01) |
| *C02F 101/20* | (2006.01) |
| *C02F 101/32* | (2006.01) |
| *C02F 103/36* | (2006.01) |
| *C07C 1/04* | (2006.01) |

(52) U.S. Cl.
CPC .......... *C01B 2203/0255* (2013.01); *C01B 2203/0283* (2013.01); *C01B 2203/062* (2013.01); *C02F 1/004* (2013.01); *C02F 2001/007* (2013.01); *C02F 1/20* (2013.01); *C02F 1/24* (2013.01); *C02F 1/283* (2013.01); *C02F 1/44* (2013.01); *C02F 1/48* (2013.01); *C02F 1/5236* (2013.01); *C02F 1/5245* (2013.01); *C02F 1/56* (2013.01); *C02F 1/66* (2013.01); *C02F 1/725* (2013.01); *C02F 3/1268* (2013.01); *C02F 2101/101* (2013.01); *C02F 2101/103* (2013.01); *C02F 2101/16* (2013.01); *C02F 2101/166* (2013.01); *C02F 2101/20* (2013.01); *C02F 2101/322* (2013.01); *C02F 2103/36* (2013.01); *C02F 2103/365* (2013.01); *C02F 2303/18* (2013.01)

(56) References Cited

FOREIGN PATENT DOCUMENTS

| | | |
|---|---|---|
| WO | 2012151605 A1 | 11/2012 |
| WO | 2016193337 A1 | 12/2016 |
| WO | 2017011025 A1 | 1/2017 |
| WO | 2017039741 A1 | 3/2017 |

OTHER PUBLICATIONS

International Search Report for related International Application No. PCT/EP2021/056728 mailed Jul. 6, 2021.

GASIFICATION AND FISCHER-TROPSCH PROCESS WASTE WATER TREATMENT

This application is a national phase of International Application No. PCT/EP2021/056728 filed Mar. 16, 2021, which claims priority to UK Patent Application No. GB2003906.1, filed Mar. 18, 2020, the disclosures of which are incorporated herein by reference in their entireties.

The present invention relates to a process for treating wastewater from a gasification process. Gasification processes are used to generate feedstock for Fischer-Tropsch (F-T) processes for the generation of hydrocarbon fuels.

The Fischer-Tropsch process is widely used to generate fuels from carbon monoxide and hydrogen and can be represented by the equation:

$$(2n+1)H_2 + nCO \rightarrow C_nH_{2n+2} + nH_2O$$

This reaction is highly exothermic and is catalysed by a Fischer-Tropsch catalyst, typically a cobalt-based catalyst, under conditions of elevated temperature (typically at least 180° C., eg 200° C. or above) and pressure (eg at least 10 bar). A product mixture is obtained, and n typically encompasses a range from 10 to 120. It is desirable to minimise methane selectivity, i.e. the proportion of methane (n=1) in the product mixture, and to maximise the selectivity towards C5 and higher (n≥5) paraffins, typically to a level of 90% or higher. It is also desirable to maximise the conversion of carbon monoxide.

The hydrogen and carbon monoxide feedstock is normally synthesis gas.

The synthesis gas may be produced by gasifying a carbonaceous material at an elevated temperature, for example, about 700° C. or higher. The carbonaceous material may comprise any carbon-containing material that can be gasified to produce synthesis gas. The carbonaceous material may comprise biomass (e.g., plant or animal matter, biodegradable waste, and the like), a food resource (e.g., as corn, soybean, and the like), and/or a non-food resource such as coal (e.g., low grade coal, high grade coal, clean coal, and the like), oil (e.g., crude oil, heavy oil, tar sand oil, shale oil, and the like), solid waste (e.g., municipal solid waste, hazardous waste), refuse derived fuel (RDF), tyres, petroleum coke, trash, garbage, biogas, sewage sludge, animal waste, agricultural waste (e.g., corn stover, switch grass, grass clippings), construction demolition materials, plastic materials (e.g., plastic waste), cotton gin waste, landfill gas, a mixture of two or more thereof, and the like. The carbonaceous material may also be Solid Recovered Fuel (SRF) which is a waste product of relatively high calorific value typically derived from paper, card, wood, textiles and plastics.

The fresh synthesis gas may be treated to adjust the molar ratio of $H_2$ to CO by steam reforming (eg, a steam methane reforming (SMR) reaction where methane is reacted with steam in the presence of a steam methane reforming (SMR) catalyst); partial oxidation; autothermal reforming; carbon dioxide reforming; or a combination of two or more thereof. In the present application, such treatment of the synthesis gas is considered to be broadly part of the F-T process and any wastewater streams resulting from such treatment are considered to be wastewater streams from the F-T process rather than from the gasification process as such.

The molar ratio of $H_2$ to CO in the fresh synthesis gas is desirably in the range from about 1.6:1 to about 2.2:1, or from about 1.8:1 to about 2.10:1, or from about 1.95:1 to about 2.05:1.

The fresh synthesis gas may optionally be combined with a recycled tail gas (eg a recycled FT tail gas), which also contains $H_2$ and CO, to form a reactant mixture. The tail gas may optionally comprise $H_2$ and CO with a molar ratio of $H_2$ to CO in the range from about 0.5:1 to about 2:1, or from about 0.6:1 to about 1.8:1, or from about 0.7:1 to about 1.2:1.

The combined FT synthesis gas feed (comprising of fresh synthesis gas combined with recycled tailgas) desirably comprises $H_2$ and CO in a molar ratio in the range from about 1.:1 to about 2.1:1, or from about 1.7:1 to about 2.0:1, or from about 1.7:1 to about 1.9:1.

The invention is concerned particularly but not exclusively with treating wastewater from a gasification process utilising Municipal Solid Waste (MSW) or Commercial and Industrial waste (C & I) as the gasification feedstock, which tends to generate wastewater with high levels of pollutants. The disposal of such wastewater and the removal of such pollutants is of pressing concern.

There is a demand for disposal of MSW and C & I waste which does not involve landfill.

There is furthermore a demand for fuel derived from renewable resources. For example, the Renewable Transport Fuel Obligation (RTFO) obligates UK suppliers of road transport fuels (such as refiners and importers) in excess of 450,000 litres annually to use a certain percentage of sustainable biofuels.

It is known to recycle wastewater from an F-T process.

Furthermore, it is known, eg from WO 2017/011025A and WO 2017/039741A to treat separate wastewater streams from gasification and F-T processes in a combined gasification and F-T installation utilising MSW as the feedstock. However, these patent applications disclose no details of the wastewater treatment or of the pollutants removed from the wastewater.

F-T wastewater treatment is disclosed in WO2016193337A1 which discussed pre-treating the waste water by distillation or steam stripping, removing residual wax by gravity and feeding the resulting pretreated waste water to a granular sludge based anaerobic bioreactor. This document pays scant regard to the treatment of salt water streams except by ion exchange or reverse osmosis.

In one aspect the present invention provides a process for treating wastewater from a combined gasification and Fischer-Tropsch (F-T) process in which aqueous effluent from the gasification is treated with alkali to produce a first wastewater stream and the first wastewater stream is treated to remove inorganic pollutants present in the aqueous effluent, and a second wastewater stream, containing water produced in the F-T process and being distinct from the first wastewater stream, is treated separately from the first wastewater stream to remove organic compounds.

The treated first wastewater stream may be discharged to the environment. The treated second wastewater stream may be reused within plant utilised in the gasification and/or F-T process.

Thus, the invention also provides a process for treating wastewater from a combined gasification and Fischer-Tropsch (F-T) process in which aqueous effluent from the gasification is treated with alkali to produce a first wastewater stream and the first wastewater stream is treated to remove inorganic pollutants present in the aqueous effluent, and a second wastewater stream, containing water produced in the F-T process and being distinct from the first wastewater stream, is treated separately from the first wastewater stream to remove organic compounds, wherein the treated first wastewater stream is discharged to the environment and the treated second wastewater stream is reused within plant utilised in the gasification and/or F-T process.

This has the advantage that the treatment of the wastewater streams is optimised. Salty inorganic wastewaters are separately treated from organic laden, non-salty wastewaters. In preferred embodiments, this allows the non-salty (fresh) water to be reused within the facility for cooling water makeup or other resource.

The first wastewater stream may for example comprise treated aqueous effluent from any one or more of a gasification zone, a partial oxidation zone, a clean-up zone and/or a hydrogen to carbon monoxide ratio shifting zone (e.g. a water gas shift zone).

In a preferred embodiment there is provided a process for the manufacture of one or more useful products (such as long chain hydrocarbons for example) comprising:
  a. gasifying a carbonaceous feedstock, preferably comprising waste materials and/or biomass, in a gasification zone to generate a raw synthesis gas;
  b. optionally partially oxidising the raw synthesis gas in a partial oxidation zone to generate partially oxidised raw synthesis gas;
  c. supplying at least a portion of the, optionally partially oxidised, raw synthesis gas to a clean-up zone to remove contaminants and provide a clean synthesis gas;
  d. optionally shifting the hydrogen to carbon monoxide ratio of the clean synthesis gas in a hydrogen to carbon monoxide ratio shifting zone to generate shifted clean synthesis gas;
  e. supplying the, optionally shifted, clean synthesis gas to an F-T reaction train to generate at least one first useful product;
  f. optionally upgrading the first useful product in a second further reaction train to generate a second useful product,
wherein aqueous effluent from one or more of stages a. to c. is treated by degassing and subsequent neutralisation and aqueous effluent from stages d and e. (and optionally also stage f.) is separately treated.

It has been found that the first wastewater stream can normally be economically treated to remove pollutants to satisfy regulatory requirements, even if the feedstock is derived from MSW or C & I waste.

Preferably the treated first wastewater stream is discharged to the environment.

Preferably the treatment comprises:
  a) degassing, and subsequently
  b) neutralising
  c) preferably clarifying, and
  d) preferably filtering
the first wastewater stream.

In a related aspect the invention provides a process for treating wastewater from a combined gasification and Fischer-Tropsch (F-T) process in which aqueous effluent from the gasification is treated with alkali to produce a first wastewater stream and the first wastewater stream is treated to remove inorganic pollutants present in the aqueous effluent, wherein the treatment comprises:
  a) degassing, and subsequently
  b) neutralising,
  c) preferably clarifying, and
  d) preferably filtering
the first wastewater stream.

The preliminary degassing step reduces the requirement for neutralisation and enhances the economics of the process. Acid gases such as $CO_2$ and $SO_2$ which would otherwise exert a caustic demand are released. This also helps maintain a lower salinity in the final treated effluent.

Additionally, the wastewater treatment of the present invention, in both its aspects, has been found to be remarkably effective in reducing heavy metal and other pollutants, even when using a relatively dirty feedstock such as MSW or C & I waste.

Preferably the process comprises the further step:
  c) oxidising dissolved or suspended components of the neutralised first wastewater stream.

This facilitates removal of heavy metals, as well as reducing the chemical oxidation demand (COD) of the wastewater.

Preferably the first wastewater stream is neutralised in a reaction zone which is agitated by an oxidising gas (eg air).

This ensures complete mixing and hence neutralisation and also enables neutralisation and oxidation in one and the same reaction vessel.

In a preferred embodiment the reaction zone is agitated by bubble aeration in the presence of a catalyst, preferably a cobalt catalyst or a ferrous catalyst, for the oxidation of one or more of: sulphites, nitrites and arsenic compounds.

Preferably the first wastewater stream is treated with activated carbon (preferably powdered activated carbon) to absorb organic compounds and/or heavy metals.

This enables a significant reduction of pollutants in an economical fashion.

Preferably the treated first wastewater stream is subjected to a dissolved air flotation process to separate spent activated carbon and other suspended solids (if present).

This process complements the treatment with activated carbon. The suspended solids will typically include heavy metal oxides.

Preferably the first wastewater stream is filtered with a sand filter, multimedia filter or membrane filter, to remove any remaining spent activated carbon and suspended solids (if present).

This feature enables virtually complete clarification of the wastewater in an economical fashion.

Preferably the first wastewater stream is treated with a coagulating agent, preferably an aluminium or iron-based coagulant and/or a flocculation-promoting polymer, to assist in the removal of suspended solids.

This feature is particularly advantageous in combination with dissolved air flotation because it agglomerates the small particles in the effluent and assists their removal by the dissolved air flotation. The coagulant also assists in the capture of heavy metals.

Preferably the first wastewater stream is subject to an air or steam stripping process, preferably under alkaline conditions, to remove ammonia. The stripped ammonia is captured and reused within the facility.

Preferably the first wastewater stream is treated with a sulphide compound. The sulphide may be an inorganic sulphide such as sodium sulphide for example, or an organic sulphide compound, preferably a heteroaromatic sulphide, most preferably an S-triazine sulphide salt, to precipitate heavy metals.

These last two features are particularly advantageous in combination when the first wastewater stream is made alkaline, because this reduces still further the solubility of precipitated heavy metal complexes.

The invention also provides a plant configured to operate the process disclosed herein. The plant may be a combined gasification and Fischer-Tropsch (F-T) plant.

Other preferred features are defined in the dependent claims.

All the preferred features can be combined in any combination.

Preferably the preferred process steps and combinations thereof are performed in the order stated above.

A preferred embodiment of the invention is described below by way of example only with reference to FIGS. 1 to 4 of the accompanying drawings, wherein.

FEEDSTOCK CONDITIONING

Figure 1:
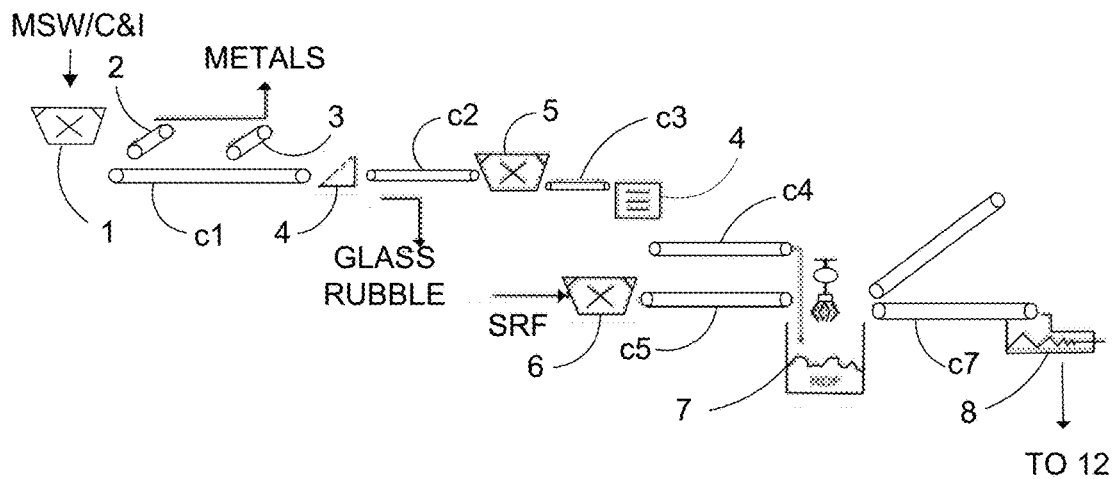
FIG. 1 is a schematic diagram of a Feedstock Conditioning Facility used to process MSW or C & I waste to a feedstock for a combined gasification and F-T process.

Referring to FIG. 1, the FCF shown receives bagged C&I and MSW Waste from a bunker (not shown) from which the bags of waste are transferred to a bag splitter 1.

The waste from bag splitter 1 is fed to a vibration conveyor c1 which passes beneath a belt magnet 2 and an eddy current rotor 3 which remove ferrous and non-ferrous metals respectively.

Oversized items are also removed at this stage.

The processed waste then passes to a density separator 4 which removes high density materials such as glass and rubble which are not combustible.

The processed waste is then transferred by a conveyor c2 to fine shredder 5 which reduces the particle size to 25 mm or less.

The size-reduced waste is then transferred by a conveyor c3 to a belt dryer 4 where excess moisture is removed. The dried waste (typical moisture content 10 wt %) is then transferred by a conveyor c4 to a bunker 7.

Bunker 7 also receives Solid Recovered Fuel (SRF) which is a waste product of somewhat higher calorific value than MSW and C&I waste and is typically derived from paper, card, wood, textiles and plastics.

The combined material from bunker 7 is then transferred by a crane to conveyor assembly c7, which feeds the processed feedstock a baler 8.

Gasification

Figure 2:
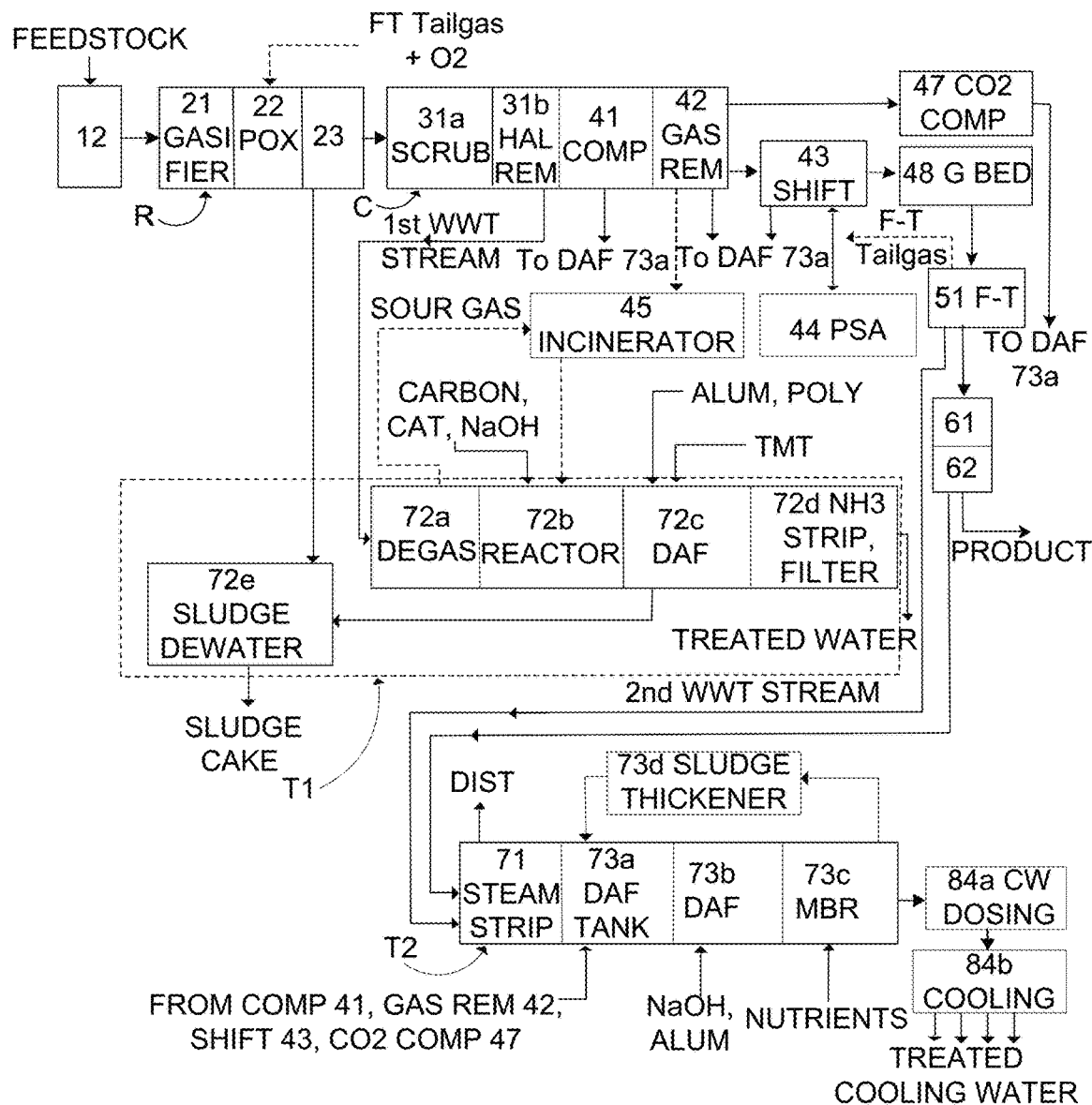
FIG. 2 is a schematic diagram of a combined gasification and F-T process utilising the feedstock generated by the FCF of FIG. 1.

Referring now to FIG. 2, baled feedstock from baler 8 is fed to a feeder 12, which pressurises the feedstock to reactor pressure and feeds it to a gasifier 21 of a reactor assembly R.

Reactor assembly R further comprises a partial oxidation (POx) reactor 22 and a radiant cooler 23.

The gasifier 21 comprises a steam reforming reactor incorporating a deep fluidised bed, the bed operating temperature being typically 600-800° C. The fluidised bed is fluidised with superheated steam and causes the carbonaceous material of the feedstock to pyrolyse and react with the steam to form hydrogen, carbon monoxide and carbon dioxide.

The syngas product of gasifier 21 is fed to partial oxidation reactor 22, which also receives F-T tailgas from an F-T reactor 51 and also oxygen. Reactor 22 is operated at a temperature above the ash melting point at a sufficient residence time to convert tars and oils and methane in the syngas to carbon oxides, hydrogen and water.

The syngas output of partial oxidation reactor 22 is fed to a cooler 23 which comprises radiant and convective cooler units. Reactor 22 also generates molten ash which is solidified in cooler 23.

The HRSG (heat recovery steam generator) has a blowdown stream of water which contains slag particles from the gasifier and PDX. The concentration of suspended solids is relatively high in this stream and it is therefore sent directly to the sludge dewatering centrifuge 72e (centrifuge rather than cyclone) for removal of the bulk of the solids before the liquid phase is co-treated with the rest of the salty water.

The cooled syngas from cooler 23 is fed to a Venturi scrubber 31a of a gas cleanup unit C, which further comprises an acid gas removal unit 31b, a compressor 41 and an acid gas removal unit 42.

Particulate matter is removed in Venturi scrubber 31a, and the resulting scrubbed syngas is passed to a halide removal unit 31b. Halide removal unit 31b comprises a packed column over which sodium hydroxide solution is passed to absorb hydrogen chloride, bromide and fluoride. The resulting 1st wastewater (WWT) stream, containing halide salts, is passed to a degassing tank 72a of a first water treatment assembly T1.

The syngas output of halide removal unit 31b is compressed in a compressor 41 and then cooled, condensing liquid (wastewater) which is then removed from the syngas and fed to a degassing tank and then on to Dissolved Air Flotation (DAF) unit 73a, discussed below.

The compressed syngas from compressor 41 is fed to acid gas removal unit 42, which operates at low temperature and high pressure and uses methanol as a solvent for removal of hydrogen sulphide, carbonyl sulphide, carbon dioxide and trace impurities such as hydrogen cyanide, ammonia, formic acid and metal carbonyls which might otherwise be detrimental to the downstream process units, in particular by poisoning the F-T catalyst. Unit 42 preferably utilises the RECTISOL™ process. The dissolved impurities are removed from the methanol solvent by stepwise flashing and are passed to an incinerator 45. The acid gas removal unit 42 also includes a mercury guard bed for absorption of mercury.

Liquid from the RECTISOL™ process in acid gas removal unit 42 and from the shift process in unit 43 is fed via a degassing tank (not shown) to DAF unit 73a. Acid gas from unit 42 is fed to incinerator 45.

Absorbed carbon dioxide is regenerated and fed to a $CO_2$ compressor 47, which discharges purified carbon dioxide to the atmosphere and also generates contaminated water which is fed via a degassing tank (not shown) to DAF 73a.

The syngas output of acid gas removal unit 42 is fed to a shift reactor 43 where the hydrogen content of the syngas is increased. Shift reactor 42 communicates with a pressure swing adsorption reactor 44 in which impurities in the hydrogen such as carbon monoxide, carbon dioxide, methane, nitrogen and argon are removed. Liquid generated in shift reactor 43 is fed to a degassing tank 72a and then on to DAF 73a.

F-T Synthesis

The syngas from reactor 43 is fed via a guard bed 48 to a Fischer-Tropsch unit 51. F-T unit 51 comprises three parallel F-T reactors in a train, each made up of an outer shell (pressure vessel) containing 4 microchannel cores. Each core is made up of multiple vertical and cross-flow microchannels.

Water generated in the F-T reaction is fed to a steam stripper 71 of a second water treatment assembly T2.

F-T products from the F-T unit 51 are fed to a liquid upgrading unit 61, which produces high quality naphtha and Synthetic Paraffinic Kerosene (SPK). The liquid upgrading unit is configured as a recycle hydrocracker to achieve full conversion of F-T materials while maximizing SPK production. This is achieved by hydrocracking, hydroisomerisation, and hydrotreating, using appropriate catalysts.

The output of liquid upgrading unit 61 is fed to a fractionator 62, which generates SPK as the main fuel product. Contaminated water from fractionation 62 is fed to steam stripper 71.

Treatment of 1st WWT

Figure 3:
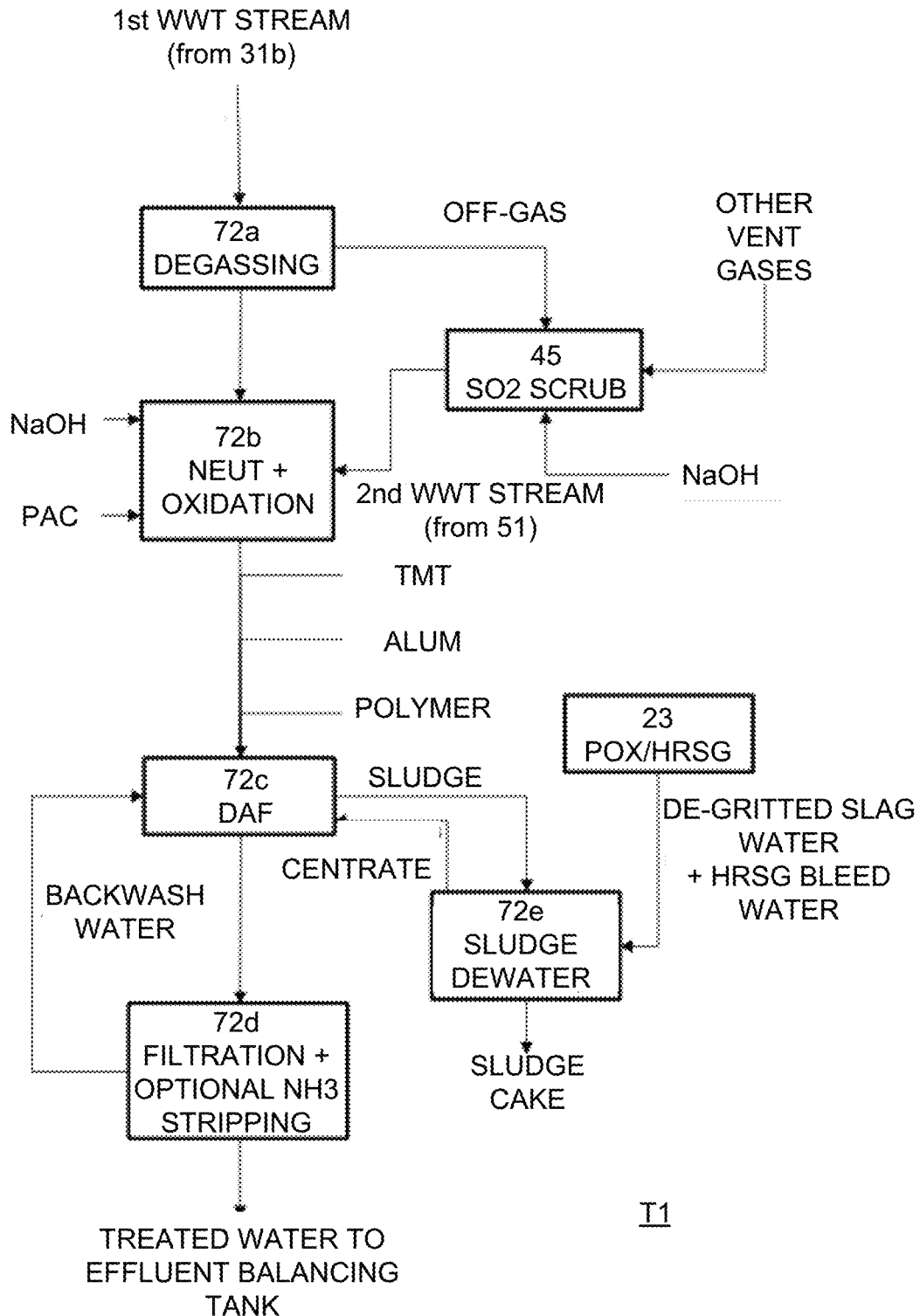
FIG. 3 is a schematic diagram of the unit T1 (apparatus 72a-72e) used for treatment of the 1st WWT (Wastewater) stream in FIG. 1.
Figure 4:
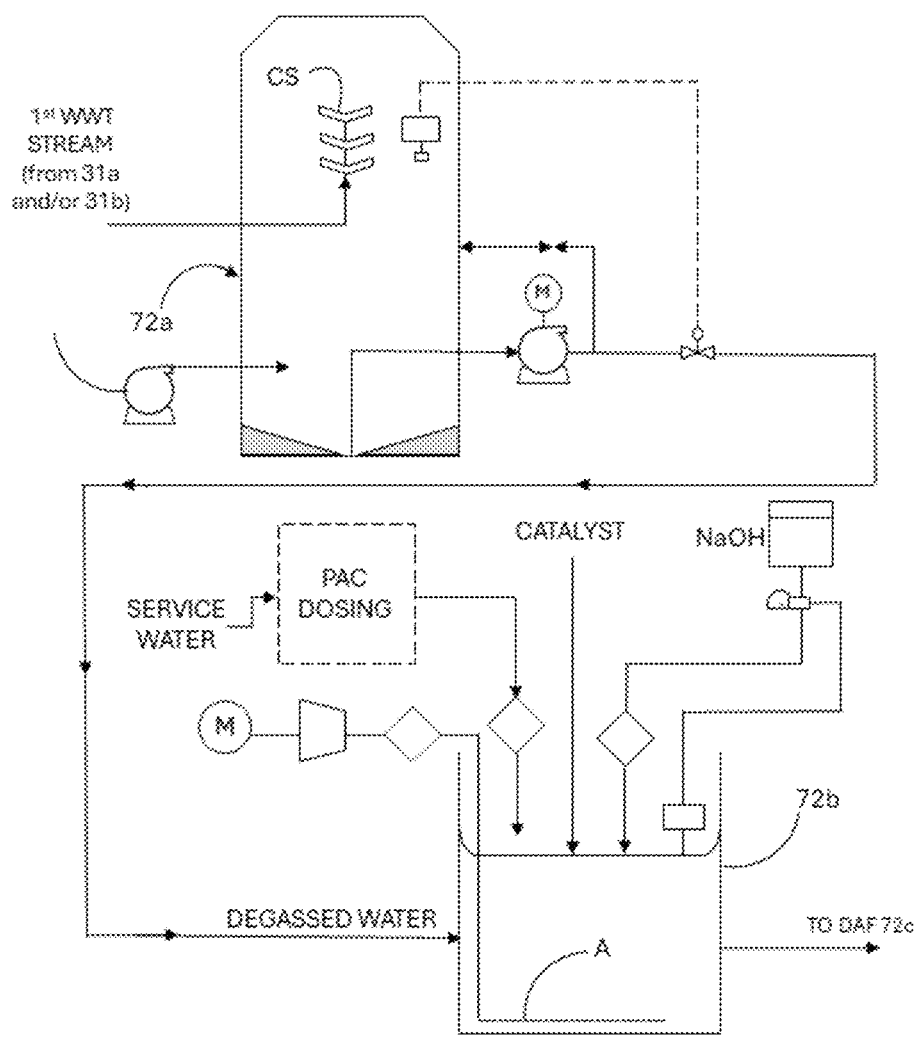
FIG. 4 is a schematic diagram showing the degassing tank and reaction tank arrangement of unit T1 in more detail.

Referring to FIGS. 2, 3 and 4, the first WWT stream from the Venturi scrubber 31a is degassed in the degassing tank 72a. This degassing tank operates under vacuum and, as shown in FIG. 4, is fitted with a multi-tiered cascade system CS to allow gases to escape naturally. The degassing tank is fitted with an externally mounted mixer pump MP to prevent suspended solids settling inside the tank. The tank is also benched, with the outlet pipework at the lowest point, to prevent solids accumulating in the tank.

Off-gas is sent to the incinerator 45, along with other process gases. In the incinerator 45, sulphurous gases are incinerated to sulphur dioxide, and this gas is then scrubbed from the incinerator flue with a sodium hydroxide solution before the vent gas is released to atmosphere.

The resulting sodium sulphite/bisulphite solution is also sent to reaction tank 72b for oxidation to sodium sulphate in the presence of a cobalt or ferrous catalyst. Reaction tank 72b is aerated by means of a coarse bubble aeration system A (FIG. 4) using two blowers. Aeration allows for the oxidation and precipitation of species such as sulphites/bisulphites, nitrite and arsenic. Neutralisation of the feed is accomplished by dosing of sodium hydroxide. The aeration also mixes the tank effectively.

The spent caustic solution contains sodium sulphite and sodium bisulphite, and this wastewater is combined with the degassed water from degassing tank 72a and fed into a reaction tank 72b where the wastewater streams are both neutralized with sodium hydroxide and oxidized by aeration. Sulphite is converted to sulphate with the aid or a cobalt or ferrous catalyst. Powdered Activated Carbon (PAC) is also dosed (see FIGS. 3 and 4) for removal of residual mercaptans following degassing, as well as certain heavy metals, phenols, cresols or other organics that could be present in the water. Cobalt (II) chloride or ferrous chloride catalyst is dosed to catalyse the oxidation of sulphite to sulphate. This tank as well as the subsequent DAF unit 72c is odour controlled.

Flows then pass to a DAF (dissolved air flotation) unit 72c. A heavy metal scavenger (TMT-15 or similar) is dosed, along with coagulant and polymer to improve the capture of heavy metals and suspended solids in the DAF unit. An aluminium based coagulant is then added to DAF unit 72c via an alum dosing pump to facilitate coagulation.

Washwater from a downstream filtration process, unit 72d, is also fed to the DAF unit 72c for clarification. It is assumed that the solids in the degassed water are finely divided soot particles, washed from the gasifier overhead product. In order to remove these very fine particles, they must be coagulated into larger flocs for easier removal by clarification and filtration.

A polymer, preferably a polyacrylamide anionic polymer, is added to the DAF unit 72c by a polymer dosing package (not shown) to facilitate flocculation.

TMT-15 (1, 3, 5-triazine-2, 4, 6-triathione sodium salt) or similar, is dosed for precipitation of heavy metals, subject to limits in the discharge permits. The floc particles are floated to the surface of the DAF unit 72c. The solids form a sludge which is continuously scraped to a sludge hopper (not shown) for transfer to the sludge dewatering centrifuge 72e which generates sludge cake for disposal.

Clarified water from the DAF unit 72c is then pumped to a filtration unit 72d. This provides continuous filtration. The type of filtration will be site specific depending on the discharge water quality requirements.

Depending on ammonia loading in the wastewater and the relevant discharge permits, an ammonia stripping system may be required between the DAF unit 72c and the filtration unit 72d. Ammonia can be stripped by dosing sodium hydroxide to raise the pH, then counter-current stripping in a packed tower with either air or steam as the stripping medium.

The high total dissolved solids (TDS) levels of the filtrate precludes its recycling as cooling water make up. Filtrate is therefore discharged via an effluent balancing tank (not shown). Here it is blended with other salty waste streams such as ion exchange softener regeneration brine and cooling tower blowdown.

The high total dissolved solids (TDS) levels of the filtrate precludes its recycling as cooling water make up. Filtrate is therefore discharged via an effluent balancing tank (not shown). Here it is blended with other salty waste streams such as ion exchange softener regeneration brine and cooling tower blowdown. In this manner the treated water from the filtration unit 72d is safely discharged to the environment.

Sludge from the DAF unit 72c is dewatered in sludge dewatering centrifuge 72e, along with PDX slag/water from unit 230. Centrate from centrifuge 72e is reprocessed in DAF unit 72c. Clarified water from DAF unit 72c is then further polished in a filtration unit 72d. Ammonia stripping with air or steam may optionally be included here if required by the pollution load and discharge permit conditions. The filters (and stripped) water is then sent to an effluent balancing tank (not shown) where it is blended with other saline streams including cooling water blowdown and softener regeneration brine, before being discharged to a suitable watercourse.

Salty wastewater from the scrubber unit 31a (1st WWT) is routed to a degassing tank 72a operating under vacuum. Referring again to FIG. 4, the tank is fitted with a multi-tiered cascade system CS to allow gases to escape naturally.

The reaction tank 72a is fitted with an externally mounted mixer pump MP to prevent suspended solids settling inside the tank. The tank is also benched, with the outlet pipework at the lowest point, to prevent solids accumulating in the tank.

A vent from the tank is routed to the incinerator 45. The degassed water is passed forward to reaction tank 72b for neutralisation, oxidation and adsorption. In the incinerator 45, sulphurous gases are incinerated to sulphur dioxide, and this gas is then scrubbed from the incinerator flue with a sodium hydroxide solution. The resulting sodium sulphite/bisulphite solution is also sent to reaction tank 72b for oxidation to sodium sulphate in the presence of a cobalt or ferrous catalyst.

Reaction tank 72b is aerated by means of a coarse bubble aeration system A using two blowers. Aeration allows for the oxidation and precipitation of species such as sulphites/bisulphites, nitrite and arsenic. Neutralisation of the feed is accomplished by dosing of sodium hydroxide. The aeration also mixes the tank effectively.

Powdered Activated Carbon (PAC) is also dosed for removal of residual mercaptans following degassing, as well as certain heavy metals, phenols, cresols or other organics that could be present in the water. Cobalt (II) chloride or ferrous chloride catalyst is dosed to catalyse the oxidation of sulphite to sulphate. This tank as well as the subsequent DAF unit 72c is odour controlled.

The range of selected contaminants that can be dealt with by first water treatment assembly T1 are given in Table 1 below.

TABLE 1

| Stream | 310-102, Gas Clean-up wastewater | 450-106, Spent Caustic | POX Slag/Water |
|---|---|---|---|
| Total suspended solids, mg/l | 2,000-20,000 | 0-100 | 100,000-500,000 |
| Total Organic Carbon, mg/l | 1-100 | 1-10 | N/A |
| Chemical oxygen demand, mg/l | 10-1,000 | 5,000-20,000 | N/A |
| Halides, mg/l | 2,000-20,000 | 0-200 | 2,000-20,000 |
| Phosphorus, mg/l | 0-20 | 0-20 | 0-20 |
| Hydrogen sulphide, sulphur dioxide, sulphite ion and bisulphite ion, mg/l as S | 100-1,000 | 5,000-30,000 | 100-1,000 |
| Ammonia as N, mg/l | 20-200 | 0-10 | 1,000-50,000 |
| Heavy metals*, mg/l | 1-100 | 0-2 | 10-100 |

*Includes As, Hg, Ni, Cd, Cu, Pb, Cr, Co, Ga, Mo, V and Zn

Treatment of 2nd WWT

Process water from F-T unit 51 and fractionation unit 62 are sent to the steam stripper 71, as noted above.

The above combined process water feed stream (2nd WWT STREAM) is first preheated and then flows down through a packed/trayed tower stripping section where it is contacted by rising steam. The flow of steam is set in ratio to the feed flow. The steam volatizes most of the organic content of the feed, yielding a bottoms stream of water with small amounts of hydrocarbons. The bottoms stream is arranged to preheat the feed stream. The bottoms stream is further cooled in an effluent cooler (not shown).

The cooled stripped water is sent for further treatment to a DAF unit 73b via a DAF feed tank 73a. DAF feed tank 73a receives wastewater streams from compressor 41, gas removal unit 42, shift reactor 43 and $CO_2$ compressor 47. These additional streams are degassed prior to entering the tank, to release entrained gases including carbon dioxide.

The above DAF assembly removes any remaining free oil from the combined stream, as well as any residual solids.

The feed is first pH corrected with sodium hydroxide, and subsequently fed into the DAF coagulation zone. A coagulant, for example aluminium sulphate, is dosed to coagulate the solids and oil droplets into larger particles in order to separate them from the water phase.

Air for the DAF process is supplied by a dedicated compressor (not shown). The air is dissolved under pressure into a recycled water flow in a contactor (not shown) and the aerated water is depressurized as it is mixed with influent feed to produce micro-bubbles of air. The bubbles attach to the coagulated particles and float them to the top of the DAF unit 73b, where they are removed as sludge by a skimmer (not shown), into a built-in sludge hopper (not shown). The sludge is removed off site by tanker.

Clarified water from the DAF unit 73b is pumped to a Membrane Bio Reactor (MBR) 73c which is fed with nutrients and converts organic pollutants to microbiological sludge, which may be transferred to a sewage works or other off-site or on site sludge treatment facilities.

The purified water from MBR 73c is dosed with anti-corrosion, anti-microbial and anti-deposition chemicals at dosing unit 84a and then fed to a cooling tower 84b where it is cooled prior to the treated cooling water being fed to units requiring cooling.

Users of cooling water include:
ash handling (not shown)
gasifier 21
gas cleanup unit C
shift reactor 43
incinerator 45
F-T unit 51
fractionation 62
wastewater treatment units T1 and T2.

The invention claimed is:

1. A process for treating wastewater from a combined gasification and Fischer-Tropsch (F-T) process in which aqueous effluent from the gasification is treated with alkali to produce a first wastewater stream and the first wastewater stream is treated to remove inorganic pollutants present in the aqueous effluent, and a second wastewater stream, containing water produced in the F-T process and being distinct from the first wastewater stream, is treated separately from the first wastewater stream to remove organic compounds, wherein the treated first wastewater stream is discharged to the environment and the treated second wastewater stream is reused within plant utilised in the gasification and/or F-T process, and wherein gasification comprises gasifying a carbonaceous feedstock comprising waste materials and/or biomass.

2. A process according to claim 1 wherein the treatment comprises:
 a) degassing, and subsequently
 b) neutralising
the first wastewater stream.

3. A process according to claim 2 wherein the treatment further comprises c) clarifying the first wastewater stream.

4. A process according to claim 2 wherein the treatment further comprises d) filtering the first wastewater stream.

5. A process according to claim 2, comprising the further step: c) oxidising dissolved or suspended components of the neutralised first wastewater stream.

6. A process according to claim 2 wherein the first wastewater stream is neutralised in a reaction zone which is agitated by an oxidising gas.

7. A process according to claim 6 wherein the reaction zone is agitated by bubble aeration in the presence of a catalyst, for the oxidation of one or more of: sulphites, nitrites and arsenic compounds.

8. A process according to claim 7 wherein the catalyst is a cobalt or ferrous catalyst.

9. A process according to claim 1 wherein the first wastewater stream is treated with activated carbon to absorb organic compounds and/or heavy metals.

10. A process according to claim 9 wherein the treated first wastewater stream is subjected to a dissolved air flotation process to separate spent activated carbon and other suspended solids.

11. A process according to claim 9 wherein the first wastewater stream is filtered with a moving bed sand filter, or a multimedia filter, or a membrane filter, to remove any remaining spent activated carbon and suspended solids.

12. A process according to claim 2 wherein the first wastewater stream is treated with a coagulating agent to remove suspended solids.

13. A process according to claim 1 wherein the first wastewater stream is subject to an air stripping process, or steam stripping process to remove ammonia.

14. A process according to claim 1 wherein the first wastewater stream is treated with a sulphide to precipitate heavy metals.

15. A process according to claim 1 wherein a second wastewater stream, containing water produced in the F-T process and being distinct from the first wastewater stream is cooled and subsequently used for cooling plant utilised in the gasification and/or F-T process.

16. A process according to claim 1 wherein gasses extracted from the first and/or the second wastewater stream are recycled to one or both of an incinerator and a sulphur scrubber.

17. A process according to claim 1 wherein a second wastewater stream, containing water produced in the F-T process and being distinct from the first wastewater stream, is subjected to:
   a) steam stripping to remove volatile organic components, and subsequently
   b) dissolved air flotation to remove less volatile organic components.

18. A process according to claim 17 wherein the second wastewater stream is treated with an aluminium-based coagulant, and/or a flocculation-promoting polymer, to remove suspended solids.

19. A process according to claim 15 wherein the second wastewater stream is passed through a Membrane Bio Reactor.

20. A process according to claim 1 wherein Commercial and industrial waste (C & I) and/or Municipal Solid Waste (MSI) are treated to form feedstock for the gasification process.

21. A process according to claim 1 for the manufacture of one or more useful products comprising:
   a. gasifying a carbonaceous feedstock, comprising waste materials and/or biomass, in a gasification zone to generate a raw synthesis gas;
   b. optionally partially oxidising the raw synthesis gas in a partial oxidation zone to generate partially oxidised raw synthesis gas;
   c. supplying at least a portion of the, optionally partially oxidised, raw synthesis gas to a clean-up zone to remove contaminants and provide a clean synthesis gas;
   d. optionally shifting the hydrogen to carbon monoxide ratio of the clean synthesis gas in a hydrogen to carbon monoxide ratio shifting zone to generate shifted clean synthesis gas;
   e. supplying the, optionally shifted, clean synthesis gas to a F-T reaction train to generate at least one first useful product;
   f. optionally upgrading the first useful product in a second further reaction train to generate a second useful product,
   wherein aqueous effluent from one or more of stages a. to c. is treated by degassing and subsequent neutralisation and aqueous effluent from stages d. and e. (and optionally also stage f.) is separately treated.

22. A combined gasification and Fischer-Tropsch (F-T) plant configured to operate the process of claim 1.

* * * * *